United States Patent [19]

Suzuki et al.

[11] Patent Number: 4,781,699
[45] Date of Patent: Nov. 1, 1988

[54] MUCUS-REMOVING DEVICE

[75] Inventors: Tatsuyuki Suzuki, Fukushima; Shoji Kawamoto, Takatsuki, both of Japan

[73] Assignee: Nissho Corportion, Osaka, Japan

[21] Appl. No.: 938,487

[22] Filed: Dec. 5, 1986

[30] Foreign Application Priority Data

Feb. 8, 1986 [JP] Japan .................. 61-17354[U]

[51] Int. Cl.$^4$ .............................................. A61M 5/315
[52] U.S. Cl. .................................. 604/218; 604/264; 604/280
[58] Field of Search ............... 128/768, 765; 604/218, 604/264, 270, 280, 281, 282, 283

[56] References Cited

U.S. PATENT DOCUMENTS

| 2,702,549 | 2/1955 | Baehr et al. | 604/218 |
| 3,394,705 | 7/1968 | Abramson | 604/280 |
| 3,426,759 | 2/1969 | Smith | 604/264 |
| 4,131,112 | 12/1978 | Kopito et al. | 604/218 |
| 4,280,500 | 7/1981 | Ono | 604/280 |
| 4,402,684 | 9/1983 | Jessup | 604/264 |
| 4,661,094 | 4/1987 | Simpson | 604/280 |

OTHER PUBLICATIONS

International Patent Application, Seed, WO82/00754, Sep. 9, 1980,

Primary Examiner—C. Fred Rosenbaum
Assistant Examiner—Mark F. Colosimo
Attorney, Agent, or Firm—Armstrong, Nikaido, Marmelstein & Kubovcik

[57] ABSTRACT

A device for removing a mucus from a uterocervical canal of an animal which comprises a tubular catheter made of a soft synthetic resin and a suction means for producing a sucking force in the inner cavity of the catheter and which is inserted in the catheter and movable lengthwise, said catheter being provided with 5 to 24 holes communicating with the inner cavity thereof, said holes distributing substantially uniformly in a portion between the tip of the catheter and a position at about 10 to 15 cm's distance from the tip of the catheter. The device has an excellent capability of removing a mucus from a cervical canal of a fertilized animal.

5 Claims, 2 Drawing Sheets

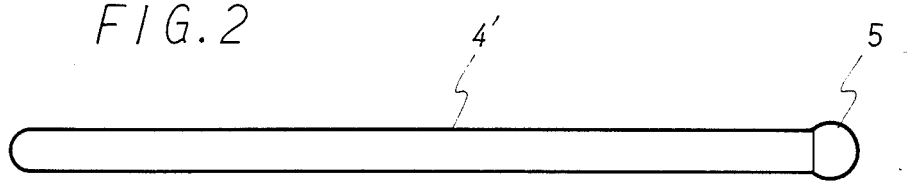
FIG.2
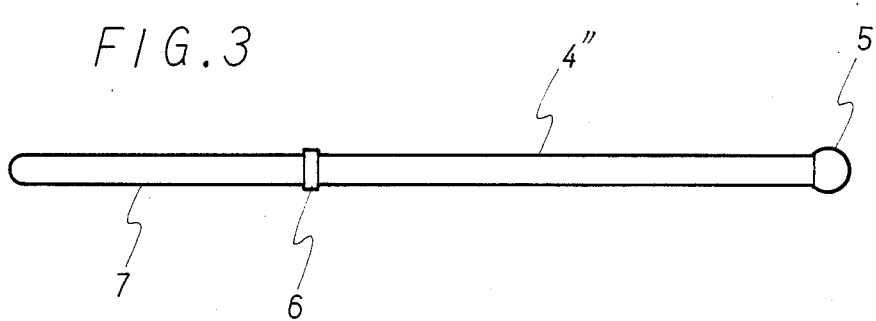
FIG.3
FIG.4 PRIOR ART

MUCUS-REMOVING DEVICE

BACKGROUND OF THE INVENTION

The present invention relates to a device for expanding a uterocervical canal of a fertilized animal and removing a mucus attached to the canal.

Generally, a cow has only 7 to 8 calves through life. For this reason, recently, a method for mass-producing superior cows in a short period by embryotransfer has been adopted to obtain a large number of cows having good blood lines behind them, a good construction and good capabilities.

Usually, recovering of embryos of cow used for transplanting is carried out by inserting a balloon catheter having many side holes in the tip portion thereof into the uterus of a cow about seven days after embryogeny and drawing embryos together with a perfusate introduced into the uterus through the catheter.

A large quantity of a mucus is present in the cervical canal of a cow about seven days after embryogeny. Therefore, when the balloon catheter is inserted into the uterus horn at such time, the mucus enters into the side holes of the balloon catheter so that the side holes are choked with the mucus, which results in difficulty in collecting embryos.

Heretofore, a rod for expanding a cervical canal as shown in FIG. 4 was used to expand a cervical canal and to remove the mucus therein. However, the mucus in the cervical canal was hardly removed by such conventional method using the cervical canal-expanding rod. Accordingly, when the balloon catheter was inserted into the uterus horn to collect embryos, the side holes of the catheter were choked with the remaining mucus and it was often difficult to collect embryos.

Embryos drawn from the uterus together with the perfusate are filtered through a wire net having a size of opening of about 70 μm to remove the perfusate and collected on the wire net. When the mucus is not removed sufficiently from the cervical canal in advance, the perfusate drawn from the uterus is frequently get mixed with the mucus. When such perfusate is filtered by using the wire net, the embryos remain on the wire net in such state that they are enclosed in the mucus, which causes an decrease of embryo-collecting rate.

It is an object of the present invention to provide a device for expanding a uterocervical canal of a fertilized animal and removing a mucus attached to the canal, which is capable of efficiently removing a mucus present in the canal.

This and other objects of the invention will become apparent from the description hereinafter.

SUMMARY OF THE INVENTION

The present invention provides a device for removing a mucus from a uterocervical canal of an animal which comprises a tubular catheter made of a soft synthetic resin and a suction means for producing a sucking force in the inner cavity of the catheter and which is inserted in the catheter and movable lengthwise, said catheter being provided with 5 to 24 holes communicating with the inner cavity thereof, said holes distributing substantially uniformly in a portion between the tip of the catheter and a position at about 10 to 15 cm's distance from the tip of the catheter.

BRIEF DESCRIPTION OF THE DRAWINGS

FIG. 2 is a plan view showing a preferred example of the suction means used in the present invention.

FIG. 3 is a plan view showing another preferred example of the suction means.

FIG. 4 is a plan view showing a conventional rod for expanding a cervical canal.

DETAILED DESCRIPTION

Figure 1:
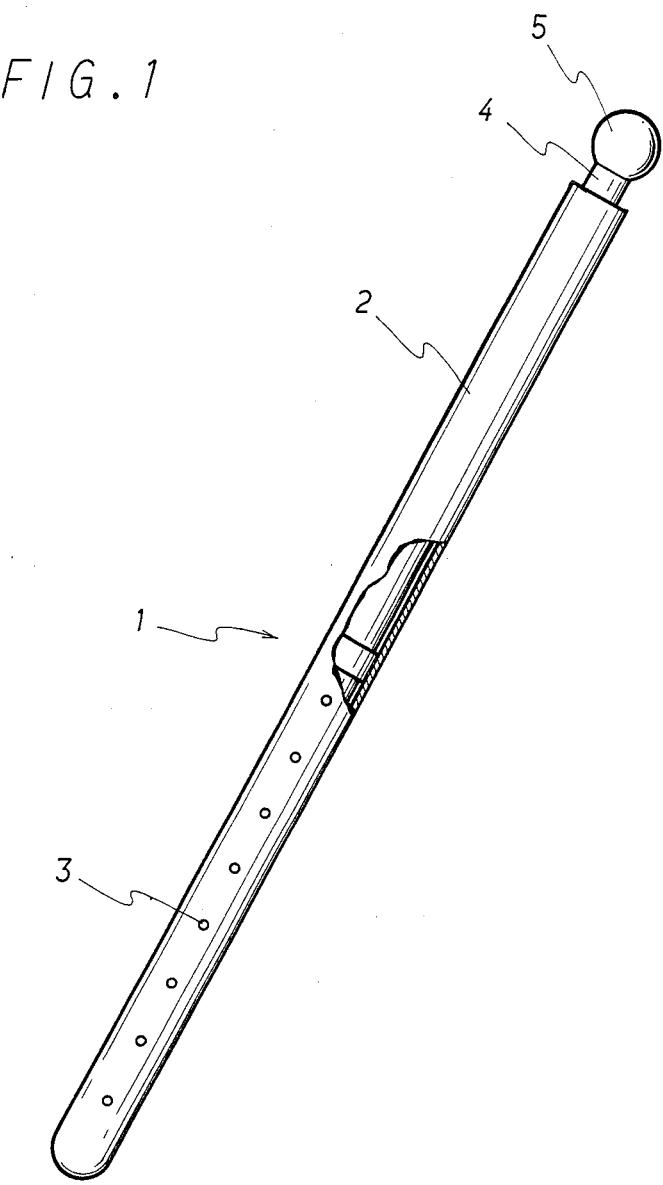
FIG. 1 is a partially broken perspective view showing an example of the device of the present invention.

Preferred examples of the suction means used in the present invention include a column-like rod having a diameter slightly smaller than the diameter of the inner cavity of the catheter and having a rounded tip, and a piston rod having an enlarged portion which comes in hermetical and slidable contact with the inner wall of the catheter.

The catheter used in the present invention is narrowed or closed at the tip portion thereof. Preferably the narrowed or closed tip portion is rounded to avoid damage of a mucus membrane of a uterus. A preferred number of holes is from 10 to 24. The material of the catheter is preferably a soft vinyl chloride resin.

A uterocervical canal of a cow is a relatively hard organ with a length of about 10 cm and having an uneven internal wall. A mucus is attached to the internal wall of the cervical canal. The mucus is secretion resembling to a white of egg and usually it is present in the form of a mass.

The function of a device for removing a mucus from a cervical canal of an animal (hereinafter referred to as "mucus-removing device") in accordance with the present invention is explained by taking as an example a device using the above-mentioned piston rod as a suction means.

When the mucus-removing device is inserted into the cervical canal of a cow and the piston rod is drawn toward an operator, a negative pressure is produced in the cavity of the catheter and the mucus is flowed into most of the holes of the catheter by action of the negative pressure just as the mucus takes strong root into the holes. When the catheter in such a state is slowly drawn from the canal, the whole of the mucus in the form of a mass is drawn together with the catheter.

Embodiments of the present invention will be explained by referring to the drawings.

Referring to FIG. 1, a mucus-removing device 1 in accordance with the present invention comprises a tubular catheter 2 having a large number of holes 3 and a suction means 4 which is inserted in the catheter 2 and movable therethrough.

The catheter 2 is made of a soft synthetic resin, preferably a soft vinyl chloride resin. The inner cavity of the catheter 2 is narrowed or closed at the tip portion thereof. The tip portion is preferably of rounded shape.

The holes 3 serve as a means for catching the mucus. The holes 3 are located in a portion between the tip of the catheter 2 and a position at about 10 to 15 cm's distance from the tip of the catheter 2 in such a manner that they distributes substantially uniformly around the catheter 2. The number of holes 3 is from 5 to 24, preferably from 10 to 24. The diameter of each hole 3 is preferably from 1 to 3 mm. The above-mentioned length of the portion where the holes 3 are provided is determined by taking into consideration a fact that usually the length of a cervical canal of a cow is about 10 cm.

The suction means 4 is provided with a grip portion 5 at one end thereof so that the suction means 4 is easily handled with a hand. Any suction means can be used as a suction means 4 as long as it provides a sufficient sucking force. A suction means which provides a sufficient sucking force and imparts to the catheter 2 a rigidity to such extent that the catheter 2 can be inserted into a cervical canal is preferably used. Preferred examples of such suction means include those shown in FIGS. 2 and 3.

The suction means shown in FIG. 2 is a column-like rod 4' having preferably a diameter slightly smaller than the diameter of the inner cavity of the catheter 2 and having preferably a rounded tip. When a catheter 2 in which the column-like rod 4' is set is inserted into a cervical canal, a water present in the cervical canal enters into a very small clearance between the inner wall of the catheter 2 and the surface of the rod 4' so that the inner cavity of the catheter 2 is sealed hermetically. When the rod 4' is gradually drawn, a negative pressure is produced in the inner cavity of the catheter 2, whereby a portion of the mucus is forced into the cavity of the catheter 2 through the holes 3.

The suction means shown in FIG. 3 is a piston rod 4" which has preferably a diameter smaller than that of the inner cavity of the catheter 2 and which is provided with an enlarged portion 6 in an intermediate area thereof, which portion comes in hermetical and slidable contact with the inner wall of the catheter 2. When a catheter 2 in which the piston rod 4" is set is inserted into a cervical canal and the piston rod 4" is gradually drawn, a portion of a mucus is forced to enter into a clearance between the inner surface of the catheter 2 and the outer surface of the rod 4" through the holes 3. Thus the mucus is firmly caught so that it is not separated from the catheter 2 when the catheter 2 is drawn. From this point of view, the clearance between the inner surface of the catheter 2 and the outer surface of the smaller diameter portion 7 of the rod 4" defined by the following formula:

(Inner diameter of the catheter—Diameter of the rod 4")

is preferably from 0.05 to 1 mm.

A combination of the action of a negative pressure produced due to the presence of the enlarged portion 6 and the above-mentioned function of the clearance between the inner wall of the catheter 2 and the outer surface of the rod 4" provides a strong sucking force.

A manner of using the mucus-removing device of the present invention will be explained by taking an example a mucus-removing device 1 using a piston rod 4" as a suction means.

A mucus-removing device 1 in which a piston rod 4" is set is inserted into a cervical canal of a cow. Then the piston rod 4" is drawn toward an operator by a length of about 10 to 20 cm, whereby a negative pressure is produced in the cavity of the catheter 2. A mucus attached to the inner wall of the cervical canal is flowed in the holes 3 by action of the negative pressure and caught in the holes 3 and the clearance between the inner surface of the catheter 2 and the surface of the rod 4" just as the mucus takes strong root into the inner cavity of the catheter 2. When the catheter 2 in such a state is slowly drawn from the cervical canal, the mucus is drawn together with the catheter 2. Thus the mucus is removed.

TEST EXAMPLE

Tests for removing a mucus from a cervical canal of a fertilized cow were carried out employing a mucus-removing device 1 in accordance with the present invention and a conventional cervical canal-expanding rod as shown in FIG. 4, respectively. Thereafter, embryos were collected by using a multi-hole type balloon catheter disclosed in U.S. patent application Ser. No. 891,996 filed on Aug. 1, 1986. The results are shown in Table 1 and Table 2.

The particulars of the mucus-removing device 1 used are as follows:
Catheter 2: The tip end is closed.
Number of hole 3: 16
Diameter of hole 3: 1.5 mm
Suction means 4: Piston rod as shown in FIG. 3.

TABLE 1

| | (Mucus-removing device of the invention was used to remove the mucus) | |
|---|---|---|
| Cow No. | Estimated number of corpus luteum | Number of collected ova |
| 1 | 16 | 16 |
| 2 | 5 | 4 |
| 3 | 10 | 10 |
| 4 | 8 | 6 |
| 5 | 28 | 27 |
| Sum | 67 | 63 |
| Ovum collecting rate (%) | | 94.0 |

TABLE 2

| | (Conventional cervical canal-expanding rod was used to remove the mucus) | |
|---|---|---|
| Cow No. | Estimated number of corpus luteum | Number of collected ova |
| 6 | 20 | 19 |
| 7 | 5 | 0 |
| 8 | 17 | 3 |
| 9 | 10 | 2 |
| 10 | 5 | 2 |
| Sum | 57 | 26 |
| Ovum collecting rate (%) | | 45.6 |

The mucus-removing device of the present invention has an excellent capability of removing a mucus from a cervical canal of an animal. When the device of the present invention is used to remove the mucus, the ovum-collecting rate is noticeably improved.

It is to be understood that the present invention is not limited to the above Example, and various change and modifications may be made in the invention without departing from the spirit and scope thereof.

In addition to the elements used in the Example, other elements can be used in the Example as set forth in the specification to obtain substantially the same results.

What we claim is:

1. A device for removing a mucus from a uterocervical canal of an animal which comprises a hollow tubular catheter having an inner cavity and made of a soft synthetic resin and a column-like rod suction means having an outer diameter slightly smaller than the diameter of said inner cavity of said tubular catheter for producing a sucking force in the inner cavity of the catheter and which is inserted in the catheter and movable lengthwise therein, said catheter being provided with 5 to 24 holes communicating with the inner cavity thereof, each of said holes having a diameter not substantially less than 1 mm and not substantially more than 3 mm, said holes being distributed substantially uniformly in a portion between the tip of the catheter and a position at about 10 to 15 cm's distance from the tip of the catheter, said column-like rod suction means, when inserted into said inner cavity adjacent the inner end of said tubular catheter and inserted substantially the length of said catheter, forming a hermetic seal between said outer diameter of said suction means and said inner cavity when said device is inserted into a mucus in a uterocervical canal and said suction means is moved lengthwise from the inner end of said tubular catheter, said hermetic seal forming a suction in said inner cavity of said hollow catheter and drawing portions of said mucus into said holes and attaching said mucus to the outer wall of said device for removal with said device from said uterocervical canal.

2. A device for removing a mucus from a uterocervical canal of an animal which comprises a hollow tubular catheter having an inner cavity and made of a soft synthetic resin and a column-like rod suction means for producing a suction force in the inner cavity of the catheter and which is inserted in the catheter and movable lengthwise therein, said catheter being provided with a 5 to 24 holes communicating with the inner cavity thereof, each of said holes having a diameter not substantially less the 1 mm and not substantially more than 3 mm, said holes being distributing substantially uniformly in a portion between the tip of the catheter and a position at about 10 to 15 cm's distant from the tip of the catheter, said suction means being a piston rod having an enlarged portion in hermetical and slidable contact with the inner wall of the catheter, said piston rod, when inserted into said inner cavity adjacent the inner end of said tubular catheter and inserted substantially the length of said catheter, forming a hermetic seal between the outer diameter of said piston rod and the inner cavity when said device is inserted into a mucus in a uterocervical canal and said piston rod is moved lengthwise from the inner end of said tubular catheter, said hermetic seal forming a suction in said inner cavity of said hollow catheter and drawing portions of said mucus into said holes and attaching said mucus to the outer wall of said device for removal with said device from said uterocervical canal.

3. The device of claim 2, wherein the inner cavity of the catheter is narrowed or closed at the tip portion of the catheter and the tip portion of the catheter is of a rounded shape.

4. The device of claim 2, wherein the number of the holes is from 10 to 24.

5. The device of claim 2, wherein the catheter is made of a soft vinyl chloride resin.

* * * * *